United States Patent [19]

Wallshein

[11] 4,144,642
[45] Mar. 20, 1979

[54] RETAINER MEMBERS FOR ORTHODONTIC BRACKETS

[76] Inventor: Melvin Wallshein, 8645 Bay Pkwy., Brooklyn, N.Y. 11214

[21] Appl. No.: 708,301

[22] Filed: Jul. 26, 1976

[51] Int. Cl.$^2$ .............................................. A61C 13/00
[52] U.S. Cl. ...................................................... 32/14 A
[58] Field of Search ........................................ 32/14 A

[56] References Cited

U.S. PATENT DOCUMENTS

| 3,772,787 | 11/1973 | Hanson | 32/14 A |
| 3,835,539 | 9/1974 | Wallshein | 32/14 A |

*Primary Examiner*—Robert Peshock
*Attorney, Agent, or Firm*—Flynn & Frishauf

[57] ABSTRACT

Retaining devices for orthodontic brackets comprise means for passing through an opening behind an orthodontic bracket or through an opening between twin-brackets and including means connected thereto for retaining an arch wire in an arch wire receiving slot of a bracket. The retaining means for passing behind an orthodontic bracket includes a bent-over arrangement which springingly wedges in a space defined between the rear of the bracket and, for example, a band to which the bracket is mounted. The retaining device also has an edge which bitingly engages the band, or the like. In the embodiment for a twin-bracket, the retaining means has a rear portion which passes through an opening defined between the brackets of the twin-bracket arrangement for engaging the bracket arrangement with spring-type action. The portion extending in the opening between the brackets may also have a bent-over portion which acts as a spring-type wedge in the space, the bent-over portion having an edge which bitingly engages the band, or the like to which the bracket arrangement is secured. The retaining devices optionally include means for connecting auxiliaries thereto.

94 Claims, 28 Drawing Figures

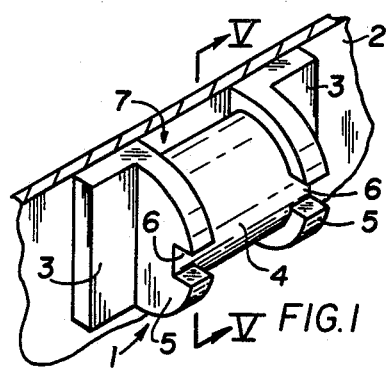
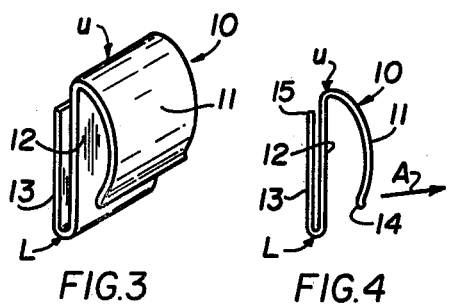
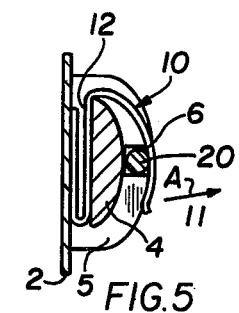
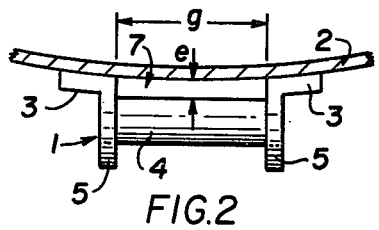
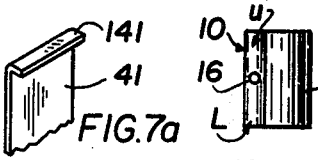
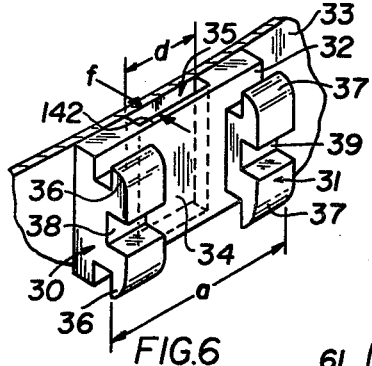
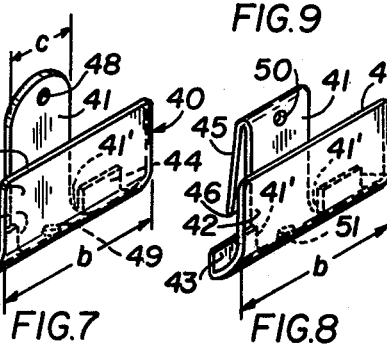
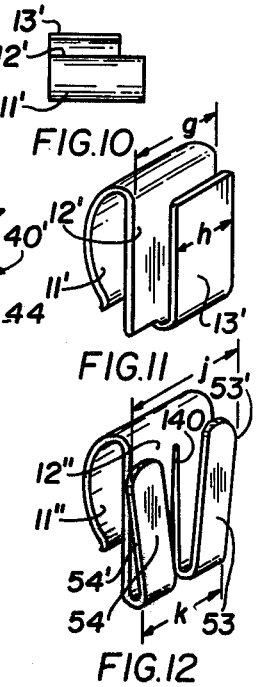
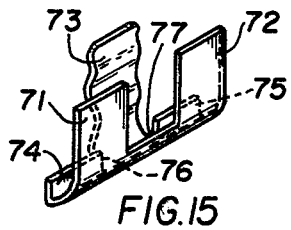
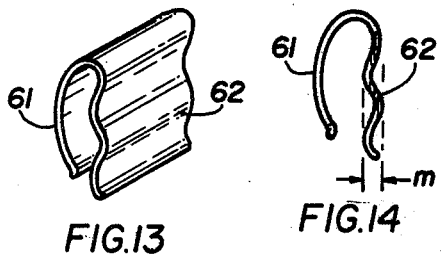
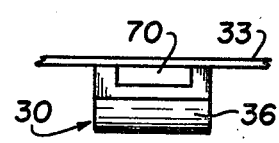
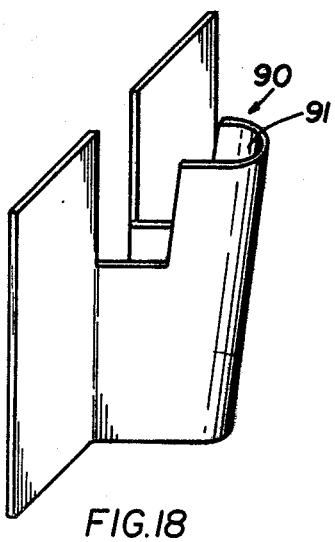
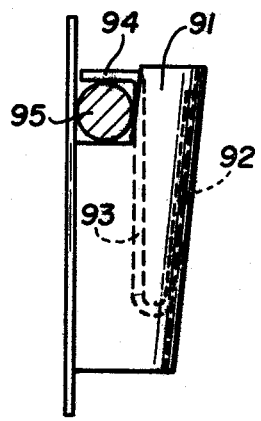
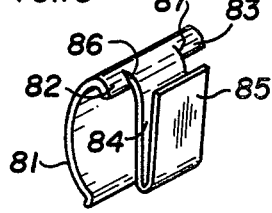

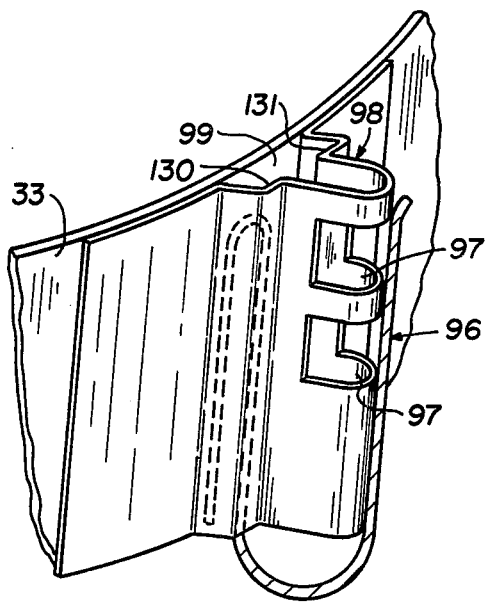
FIG.20
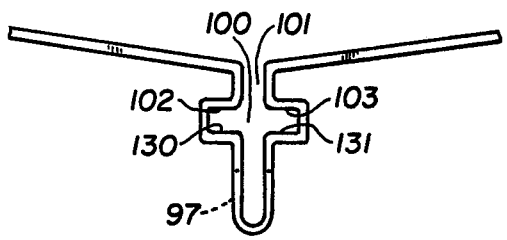
FIG.21
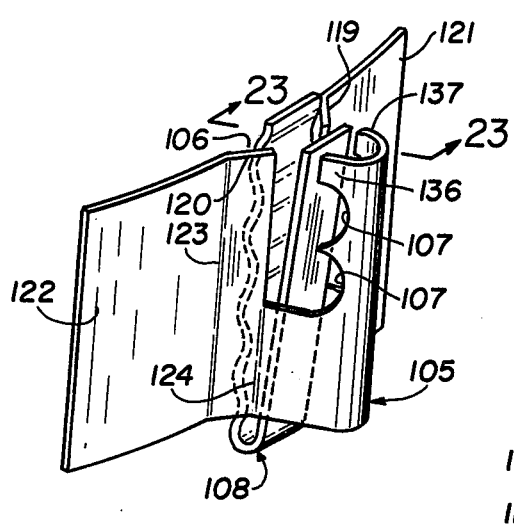
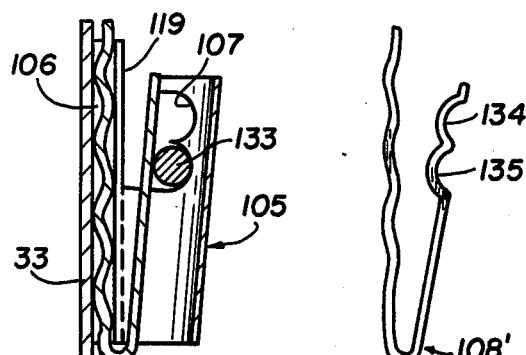
FIG.23  FIG.24
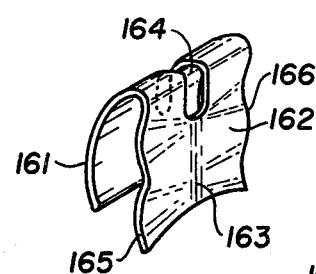
FIG.27
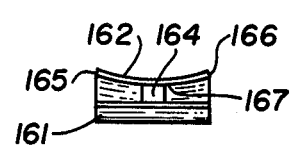
FIG.28
FIG.25
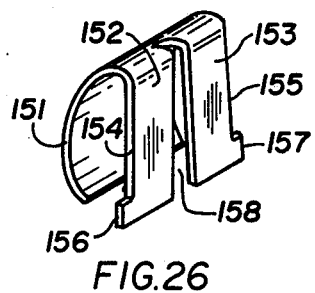
FIG.26

RETAINER MEMBERS FOR ORTHODONTIC BRACKETS

The present invention relates to improvements in orthodontic brackets, and more particularly to retainer members which are particularly adapted to retain arch wires in orthodontic brackets.

An object of the present invention is to provide an easily used, inexpensive to manufacture and highly reliable retainer member for use with orthodontic brackets for retaining an arch wire, or the like, in engagement with the orthodontic bracket.

It is a further object of the invention to provide retainers for orthodontic brackets which may also be used to mount auxiliaries in a simple and expedient manner, without requiring modification to the orthodontic bracket, and without requiring substantial increases in cost in the retainer member.

A still further object of the present invention is to provide a retaining device which is completely removable from the orthodontic bracket in a simple and expedient manner.

SUMMARY OF THE INVENTION

In accordance with the present invention, retaining devices for orthodontic brackets comprise means for passing through an opening behind the body of an orthodontic bracket or through an opening between twin-brackets, and including means connected thereto for retaining an arch wire in an arch wire receiving slot, or the like, of a bracket. The retaining means for passing behind an orthodontic bracket includes a bent-over, generally U-shaped arrangement which springingly wedges in the opening behind the body of the bracket. In a preferred arrangement, the retaining device also has a free edge which bitingly engages a band, or the like, which is used to mount the bracket to a tooth and which defines a wall of the opening. In a twin-bracket arrangement, the rear portion of the retaining means passes through an opening defined between the brackets. This rear portion also prevents sidewise movements of the retaining device relative to the twin-bracket. The portion extending in the opening between the brackets may also have a bent-over, generally U-shaped portion, which acts as a spring-type wedge in the opening and this portion may have a free edge which bitingly engages a band, or the like. The retaining devices optionally include means for connecting auxiliaries thereto.

According to a further feature of the present invention, the engaging means for the arch wire retaining device comprises a rear member which passes through the slot behind the orthodontic bracket and which has a wavy or undulating shape. The peak-to-peak distances between opposing peaks should preferably be slightly greater than the width of the slot so that the undulating portion will springingly engage in the slot. Alternatively, according to a still further feature of the invention, the portion of the retaining device which passes through the slot may be split so that it forms two spaced legs, the two spaced legs being sprung apart so that they must be springingly sprung toward each other to pass through the slot, thereby locking the retaining device in the slot.

Other features and aspects of the present invention will become more apparent from the following description of specific embodiments of the invention.

BRIEF DESCRIPTION OF THE DRAWINGS

FIG. 1 is a perspective view of a typical orthodontic bracket with which the retainers of the present invention may be used;

FIG. 2 is a top view of the orthodontic bracket of FIG. 1 shown mounted on a band which is adapted to be secured to a tooth;

FIG. 3 is a perspective view of a retainer member according to a first embodiment of the present invention;

FIG. 4 is a side view of the retainer member of FIG. 3;

FIG. 5 shows the retainer member of FIGS. 3 and 4 mounted to a bracket of FIG. 1;

FIG. 6 illustrates a typical twin orthodontic bracket for use with another embodiment of a retainer device according to the present invention;

FIG. 7 illustrates a retainer device for use with the bracket arrangement of FIG. 6;

FIG. 8 illustrates a retainer device modified from the form illustrated in FIG. 7;

FIG. 9 illustrates a modification of the embodiment of FIGS. 3 and 4;

FIG. 10 illustrates a further modification of the invention whereby the rear portion of the retaining device is reduced in size so that auxiliaries may be passed through the slot of the bracket;

FIG. 11 is a rear perspective view of the embodiment of FIG. 10;

FIG. 12 illustrates a further modification of the invention;

FIG. 13 illustrates a still further retaining device according to the present invention;

FIG. 14 is a side view of the retaining device of FIG. 13;

FIG. 15 illustrates a still further embodiment of the present invention for use with twin brackets;

FIG. 16 and 17 illustrate a bracket and retainer device, respectively, different from that of FIGS. 1-5;

FIGS. 18 and 19 are perspective and side views, respectively, illustrating the invention as applied to a Begg or Lite wire bracket;

FIG. 20 illustrates another bracket with which the present invention is useful;

FIG. 21 illustrates a modification of the bracket of FIG. 20;

FIGS. 22 and 23 are perspective and side views, respectively of another bracket with which the present invention is useful;

FIGS. 24 and 25 are side views of further retaining devices of the present invention;

FIG. 26 is a perspective view of another embodiment of the present invention; and FIGS. 27 and 28 are perspective and bottom views, respectively, of yet another embodiment of the invention.

DETAILED DESCRIPTION OF ILLUSTRATED EMBODIMENTS

FIG. 1 illustrates a typical orthodontic bracket 1 mounted on a band 2 which is adapted to be secured to a tooth in a conventional manner. The bracket 1 may alternatively be mounted directly to a tooth. The bracket 1 comprises tabs or lugs 3 which are secured to the band 2 by means of soldering, welding, or any other suitable technique. The bracket 1 also includes a central body portion 4 between protruding side members 5 which have arch wire receiving slots 6 therein. The body portion 4 is mounted to the side portions 5 so that a space 7 is provided between the rear wall of the body portion 4 and the bracket 2, as illustrated in FIGS. 1 and 2.

A removable retainer member for retaining, for example, an arch wire in the slots 6 of the bracket 1 is illustrated in FIGS. 3-5. The retainer device 10 has a front portion 11 which is adapted to pass over the front of the body portion 4 of the bracket as illustrated in FIG. 5 in order to retain an arch wire 20 in the arch wire receiving slots 6 of the bracket. Integral with the front portion 11 of the retainer member 10 is a rear portion 12 which is adapted to pass in the space 7 between the rear surface of the body portion 4 and the band 2. The rear portion 12 has an integral member 13 which is turned back on portion 12 as illustrated in FIGS. 3-5. The retainer device 10 is preferably made of a spring-type metal or any other resilient material which has sufficient rigidity to retain an arch wire 20 in the slots 6 as illustrated in FIG. 5. The retainer device 10 is configured such that the front portion 11 must be sprung outwardly in the direction of the arrow A in FIGS. 4 and 5 in order to springingly engage same over the body portion 4 of the bracket, as shown in FIG. 5. In order to aid in passing the front portion 11 over the front part of the bracket 1, an outwardly turned portion 14 may be provided as illustrated in FIG. 4.

The rear portions 12 and 13 of the retaining device, of U-shape, 10 pass through the space 7 provided between the central portion 4 of the bracket and the band 2. Part 13 is sprung outwardly away from portion 12 so that when parts 12 and 13 of the retaining device is inserted in space 7, the part 13 is springingly forced toward part 12. Thus, when the retaining device is mounted to the bracket as shown in FIG. 5, the part 13 of the retaining device is springingly biased to the left away from the portion 12 so as to wedge the portions 12 and 13 in the space 7 between the band and the rear surface of the central portion 4 of the bracket. This spring-type wedge engagement provides excellent retention of the retaining device 10 to the bracket, even against forces in the upward direction with reference to FIG. 5. Since the part 13 is biased away from part 12 in the engaged state, the edge 15 of part 13 bitingly engages the band 2 so as to further prevent the retaining device from being inadvertently forced out of engagement with the bracket.

In addition to the firm engagement of the retaining device 10 with the bracket 1, the retaining device 10 has a further advantage in that several points of flexure are provided so that when the front portion 11 of the retaining device 10 is springingly moved in the direction of the arrow A in FIGS. 4 and 5, for example when installing an arch wire 20 in the slots 6, the flexing forces applied to the retaining device 10 are more evenly distributed thereover to prevent breakage thereof. For example, referring to FIG. 4, when the portion 11 is flexed in the direction of the arrow A, the retaining device 10 will flex, for example, at the upper curved portion U as well as at the lower curved portion L. Thus, since flexure forces are more evenly distributed over the length of the retaining device 10, the retaining device can be expected to have a longer useful life. In the event of breakage of the retaining device 10, it may be relatively easily removed and easily replaced. Since no specially designed intricate locking means is required, the retaining device 10 may be inexpensively manufactured and may be used with conventional brackets.

The retaining device 10 may be provided with a hole in the lower portion L for the attachment of auxiliaries to the bracket, as illustrated in FIG. 9 which is a bottom view of the retaining device 10 of FIG. 3. The hole 16 may be any size or shape, as desired, and is adapted to receive auxiliaries therethrough for connection to the bracket, thereby increasing the usefulness of the retaining device. Auxiliary connecting means can be provided in other places on the retaining device 10, as desired.

FIG. 6 generally illustrates a twin bracket arrangement with which a modified bracket retainer according to the present invention is provided. In FIG. 6, the brackets 30,31 are shown spaced apart by a distance which is exaggerated in FIG. 6 for ease of illustration. The brackets 30,31 are mounted to a bracket plate 32 which in turn is mounted to a band 33 which is adapted to be secured to a tooth. The bracket plate 32 has a portion 34 which is cut out in the rear so as to define a space 35 with the band 33. The space 35 has a width "d" as shown in FIG. 6. The brackets 30,31 have respective wings 36,37 and respective arch wire receiving slots 38,39.

FIG. 7 illustrates one embodiment of a retaining device 40 for use with the bracket arrangement of FIG. 6. The retaining device 40 has a first upwardly extending portion 41 which is adapted to pass through the opening 35 between the bracket plate 32 and the band 33. The retaining device 40 further has a front portion 42 which is adapted to pass around the front faces of the brackets 30,31 so as to cover the respective arch wire receiving slots 38,39. The front portion 42 may be split as shown in FIG. 15. The front portion 42 has turned portions 43,44 which are bent back relative to the front portion 42 and which engage behind the wings 36,37 of the brackets 30,31, respectively. Preferably, the retaining device 40 is fabricated of a single piece of spring-type metal, or the like. In the form illustrated in FIG. 7, the portion 41 and the front portion 42 are biased toward each other so that in order to mount the device 40 on the twin brackets of FIG. 6, the upwardly extending rear portion 41 must be sprung away from the front portion 40 to provide spring-type engagement when the retaining device 40 is mounted on the twin bracket arrangement of FIG. 6. The bent over portions 43,44 are separated from the upwardly extending portion 41 along lines 41' to permit portion 41 to be inserted in the space 35. The bent over portions 43,44 may also be biased toward the front portion 42 so that they will springingly engage the wings 36,37 of the brackets when the retaining device 40 is mounted to the brackets.

The upwardly extending portion 41 (FIG. 7) is preferably dimensioned so as to have a width "C" which is substantially equal to or slightly less than width "d" of the bracket opening 35 (FIG. 6) to prevent sidewise movement of the retaining device 40 relative to the bracket assembly when installed thereon. If the width "C" of the upwardly extending portion 41 is made slightly larger than the width "d" of the bracket opening 35, the upwardly extending portion will be wedged diagonally in the opening 35. If the upwardly extending member 41 has a width "C" which is substantially equal to the distance between diagonally opposed corners of the opening 35, the upwardly extending member 41 will be tightly wedged between diagonally opposed corners of the opening 35 to tightly locate the retaining device relative to the bracket without any further engaging mechanisms.

FIG. 8 shows a modified form of the retaining device of FIG. 7. In FIG. 8, the upwardly extending member 41 has an integral downwardly bent over part 45 which is similar in function to the portion 13 of the retaining device of FIGS. 3-5. When the retaining device 40' of FIG. 8 is mounted to the twin brackets of FIG. 6, the portion 45 which is normally biased away from portion 41 is resiliently sprung towards portion 1 so as to provide firm frictional engagement of the portions 41, 45 in the space 35 defined by the bracket plate 32. Additionally, the lower edge 46 of rear portion 45 bitingly engages the band 33 to further enhance engagement of the retaining device 40' to the bracket structure.

In the embodiments of FIGS. 7 and 8, the width "b" of the retaining devices is generally substantially equal to the width "a" of the twin bracket, although in many instances, the dimension "b" is somewhat less than the dimension "a." The portion 42 has a vertical height sufficient so that when the retaining device is mounted on the twin bracket, the upper edge 47 of the front portion 42 will extend above the arch wire receiving slots 38,39 to retain a respective arch wire in the receiving slots 38,39. Other dimensional configurations could also be used, as desired.

In the embodiment of FIG. 7, a hole or opening 48 may be provided which extends above the upper extremity of bracket plate 32 for the purpose of attaching auxiliaries to the bracket arrangement. Alternatively, or additionally, a hole 49 may be provided in the lower portion of the retaining device 40 for the connection of auxiliaries. In FIG. 8, similar holes 50 and 51 may be provided for the connection of auxiliaries. In FIG. 8, the rear portion 45 also may have a hole (not shown) in registration or alignment with the hole 50 to facilitate connection of auxiliaries. Other auxiliary connection means could be provided, as desired.

In an embodiment similar to FIG. 7, the upper free end of member 41 may have a bent over portion 141, such as shown in FIG. 7a, and member 41 may be biased toward member 40 so that bent over portion 141 snaps into engagement over the upper surface portion 142 of the bracket assembly after it passes upwardly through opening or passageway 35.

FIGS. 10 and 11 illustrate another embodiment of the retaining clip of the present invention which is similar to the embodiment of FIGS. 1-5, but which has a different means for enabling auxiliaries to be connected to the bracket. In FIG. 10, which is a top view of FIG. 11, the width of the rear portion 13' is reduced relative to the width of the front portion 11'. That is, the width "h" of the rear portion 13' is less than the width "g" of the front portion 12' and of the opening 7 (FIG. 2). This provides a space in the opening 7 through which auxiliaries can be passed and positively mounted to the bracket. In other respects, the retaining device of FIGS. 10 and 11 operates similarly to the device of FIGS. 3-5.

FIG. 12 illustrates a further modification of the invention wherein the rear portion of the retaining device is formed of two spaced members 53,54 which are integral with the intermediate portion 12" and front portion 11" of the retaining device. In the arrangement of FIG. 12, the members 53,54 are preferably located and dimensioned such that the distance "j" between the outermost vertical extremities thereof is slightly greater than the width "g" of a bracket opening (for example as shown in FIG. 2). Thus, when inserting the members 53,54 in, for example, a bracket opening 7, the members 53,54 are springingly moved toward each other and the outward biasing effect locks the members 53,54 in the opening 7 with the side vertical edges of members 53,54 in engagement with side walls of the opening 7. The dimension "k" is preferably just equal to or less than the width "g" of a bracket opening. Thus, the outer edges 53',54' of members 53 and 54 are slightly tapered. In addition, the members 53,54 preferably springingly wedge in the bracket opening in the same manner as members 12 and 13 in the embodiment of FIGS. 3-5.

The leg members 53,54 can be formed in portion 12" rather than being bent over from portion 12". In this event, the free ends of legs 53,54 may have tapered outer edges to facilitate insertion in a passageway 7 of a bracket arrangement. In either case, the space between legs 53,54 can be used to accommodate auxiliaries. Additionally a slot 140 can be formed in member 12" to add additional spring engagement between the vertical outer surfaces of member 12" and the side surfaces of opening 7.

FIG. 13 illustrates a still further embodiment of the present invention wherein the retaining device has a front surface 61 (similar to the surface 11 of FIGS. 3-5) and a rear surface 62 which is wavy as illustrated in FIG. 13 and as more clearly illustrated in FIG. 14 which is a side view of the retaining device of FIG. 13. In this embodiment, the peak-to-peak distance "m" is slightly larger than the depth "e" of the opening 7 behind the orthodontic bracket. The retaining device of FIGS. 13 and 14 is made of springy material so that upon insertion of the rear portion 62 into the bracket opening 7, the rear surface portion 62 flexes due to abutment of the oppositely directed peaks against opposing surface portions of the opening 7 so as to springingly lock the retaining device in position on the bracket. The retaining device of FIG. 13 and 14 may also include holes, or the like, for connection of auxiliaries to the bracket.

FIG. 15 illustrates an embodiment of a retaining device similar to that of FIG. 7, but utilizing the retention concept described above with respect to FIGS. 13 and 14. In FIG. 15, the front portion of the retaining device is comprised of members 71,72, each of which engage front surface portions of respective spaced brackets 36,37 (FIG. 6). The upwardly extending portion 73 is wavy (similar to the rear portion 62 of FIGs. 13 and 14) so that upon insertion of the upwardly extending portion 73 in the bracket opening 35, the oppositely directed peaks of the wavy portion will springingly engage opposing surface portions of the opening 35 to firmly lock the retaining device in position on the bracket arrangement. The retaining device of FIG. 15 also includes turned under portions 74,75 to engage the wings of the brackets in order to stabilize the arrangement to improve the retention characteristics on the bracket. Cuts 76, 77 are provided between the turned under portion 74,75 and the upwardly extending portion 73 to enable the upwardly extending portion to flex rearwardly for insertion in the bracket opening 35, or the like.

FIGS. 16 and 17 illustrate a bracket and retaining device, respectively, somewhat modified from the earlier described embodiments. The bracket 30 of FIG. 16 is similar to the brackets 30,31 of FIG. 6. The bracket 30 of FIG. 16 has a slot 70 defined at the rear surface thereof and through which a retaining device is to pass and be springingly engaged. In FIG. 17, a retaining device for use with the bracket of FIG. 16, includes a front surface 81 having turned or bent over portions 82,83 which are adapted to engage the wings 36 of the bracket 30. A rearwardly extending portion 84 which is narrowed down with respect to the front portion 81 is provided, and has an integral upwardly extending rear member 85 which forms, together with the member 84, a generally U-shaped configuration. Cuts 86, 87 are provided to enable the portion 84 to be more freely flexible relative to the bent over portions 82,83 to facilitate insertion of the retaining device in the opening of the bracket. The operation of the retaining device of FIG. 17 is identical to that of FIGS. 3–5 and should be apparent. The rear engagement portion of the retaining device of FIG. 7 may take the form as illustrated in FIGS. 13–15.

FIG. 18 illustrates a typical Begg or Lite wire type bracket and FIG. 19 shows a side view thereof with a retaining device according to the present invention mounted therein. The bracket of FIGS. 18 and 19 is preferably made of a single piece of stamped out metal which is formed or bent to the shape shown. The bracket 90 has an opening 91 for receiving an engaging portion of a retaining device, as shown in FIG. 19. The retaining device has rear portions 92, 93, which form a generally U-shaped configuration, which is engageable in the opening 91 in the same manner as the retaining devices of FIGS. 3–5. The portions 92,93 may be replaced with a rear portion which is wavy in nature similar to those shown in FIGS. 13 and 14. The retaining device further has a pin portion 94 which extends over the arch wire 95 to retain same in the arch wire opening of the bracket.

FIG. 20 illustrates another Begg type bracket with a retaining device (shown partially in section for ease of illustration) installed thereon. The retaining device 96 retains an arch wire, or the like, in the arch wire receiving openings 97 of the bracket 98. The bracket 98 partially defines a rear opening 99 which extends throughout the height thereof for reception of the rear portion of a retaining device 96. The bracket 98 is preferably made of a metal stamping which is bent or formed to the shape shown. The surfaces of opening or passageway 99 against which the retaining device 96 wedges are defined by shoulders 130, 131 of the bracket and a surface of the band 33, or the like on which the bracket is mounted.

FIG. 21 illustrates a modification of the bracket of FIG. 20 wherein the opening 99 is replaced by an opening 100 having a narrowed down portion 101 for reception of auxiliaries, or the like. The rear portion of the retaining device of the present invention is retained within the opening 100 by means of wall portions 102, 103, as well as shoulders 130, 131.

FIG. 22 illustrates a further novel arrangement with which the retaining device of the present invention is useful. The bracket 105, preferably made of a formed metal stamping, has bent out portions 119, 120 which define two elongated passageways 106 (only one being referenced in FIG. 22 for ease of illustration) for receiving the rear portion of a retaining device 108 of the present invention. The bent out portion 120 is formed by bending on bend line 123 and the body portion of the bracket bends out on bend line 124. The rear portion of retaining device 108 is engaged at its edges in passageways 106 and is springingly wedged between portions 119, 120 and a surface of a band 33 (FIG. 23) or the like on which the bracket is mounted. The front portion of the spring-type retaining device 108 retains one or more arch wires 133 in the arch wire receiving channels 107, as shown in the side view of FIG. 23. The rear portion of the retaining device 108 is shown in FIG. 23 as being similar to that of FIGS. 13–15. However, the rear portion could be the same as shown in FIGS. 3–5. As shown in FIG. 24, the front portion of the retaining device 108' could have depressions 134, 135 to conform with the sahpe of arch wires or the like. The width of the retaining device 108' could be small enough so that the front portion thereof fits between faces 136, 137 of the bracket body.

As should be apparent, the retaining devices of the present invention are preferably made of spring-type metal which provides the desired resiliency to enable the devices to be easily inserted on a bracket arrangement, and which have the desired springiness to provide tight engagement to the bracket, but which still permits easy removability therefrom.

FIG. 25 is a side view of another embodiment wherein a retaining device 110 has a front surface portion 111 which is adapted to retain an arch wire in an arch wire receiving slot of a bracket, in the manner similar to portion 11 in FIGS. 3–5. The rear portion 112 of the retaining device has a roughened or serrated surface 113. The rear portion 112 is designed such that the peak-to-peak distance between the serrations on opposing sides of the rear portion 112 is slightly greater than the depth (e in FIG. 2, for example) of a passageway behind the bracket so that the retaining device 110 is press fit therein. The rear portion 112 may have a central slit, for example as shown in FIG. 12 or in the following FIG. 26, so that its outside end surfaces can grip against the narrow surfaces of, for example, opening or passageway 7.

FIG. 26 illustrates a modification of the arrangement of FIG. 12 wherein the rear portion of the retaining device comprises legs 152 and 153 which are integral with the front portion 151. The front portion is similar in function and appearance to front portion 11 of FIGS. 3–5. The legs 152, 153 have outer surfaces 154, 155 which are designed to bear against the side or narrow surfaces of opening 7 of a bracket. The legs 152, 153 have respective protrusions 156, 157 at the free ends thereof. The legs 152, 153 and protrusions 156, 157 are dimensioned such that the legs must be pressed toward each other to reduce the size of space 158 when inserting same in an opening of a bracket. The legs and protrusions are dimensioned, and are made of material sufficiently resilient, such that when the protrusions 156, 157 pass out of opening 7, the protrusions snap outwardly and retain the retaining device in position. The opening 158 between legs 152, 153 is convenient to provide a space for auxiliaries, and the opening 158 may extend to the front surface portion 151 of the retaining device as shown in FIG. 26.

FIGS. 27 and 28 show rear perspective and bottom views, respectively, of a further modified retaining device which is particularly convenient for providing space for auxiliaries. The retaining device of FIGS. 27 and 28 has a front portion 161 which is similar to front portion 11 of the embodiments of FIGS. 3–5. The rear portion 162, which is integral with the front portion 161, is bowed as indicated in FIGS. 27 and 28, which bowde shape may be conveniently obtained by bending substantially along a bend line 163 illustrated in FIG. 27. A slot or opening 164 is optionally provided in the upper end or bent over portion of the retaining device to render the bend 163 to be more easily made and to enable auxiliaries to more easily pass between the central portion 163 of rear member 162 and a surface which defines an opening, for example 7, of a bracket. In the embodiment of FIGS. 27 and 28, the retaining device is preferably made of a spring-type metal such that the end surfaces 165, 166 will bear against a surface defining the opening 7 of a bracket and the central surface portion 167 will bear against an opposing surface defining the opening 7 and the rear portion 162 will be caused to flex to be resiliently engaged in the opening. The distance between the rear surface portion 167 and the edges 165, 166, in the direction perpendicular to the plane of front portion 161, is slightly greater than the depth "e" of a bracket opening 7 (see FIG. 2) to provide appropriate spring-type engagement. The edges 165, 166 may be tapered at their free or leading ends, or may be otherwise bent back to facilitate insertion of the rear portion 162 in the opening of a bracket.

As should be apparent from the above discussion of specific embodiments, a feature of the present invention is that retaining devices include a means, for example the side surfaces of the rear portions, for engaging side surfaces of an opening to prevent mesial-distal movements of the retaining device relative to the bracket. Additionally, and simultaneously, means are provided, for example the slots or the bowde configuration of the rear portion 163, to enable auxiliaries to be connected to a bracket arrangement in a simple and expedient manner, without requiring complex or additional devices.

It should be clear that the embodiments illustrated and described are merely exemplary and that various modifications and alterations can be made thereto. Also, it should be clear that various features of the various different embodiments may be used in any desired combination and with any type of bracket having openings, passageways, channels, or the like through which such a retaining device may pass.

Throughout the drawings, it should be clear that the various features of the invention are not, in most instances, drawn to scale for ease of description. For example, in FIGS. 13-15 the waviness of the rear portion of the retaining device may be more or less shown, depending upon the particular application.

The present invention, as should be apparent from the above, provides an easily removable retaining device which is simple in construction, which will have a long useful life, and which provides highly reliable engagement with a bracket or bracket assembly. Still further, the retaining devices according to the present invention may be conveniently used to attach auxiliaries to the bracket arrangement. The bracket or bracket assembly need not be specially designed — standard units could be used.

While the invention has been described above with respect to specific embodiments, it should be clear that various modifications and alterations can be made within the scope of the appended claims.

I claim:

1. An orthodontic bracket arrangement comprising:
   a bracket body having means for receiving an arch wire, means for connecting said bracket body to a tooth, and means defining an elongated passageway between at least a portion of the bracket body and the tooth mounting means; and
   a retainer member slidably engageable with said bracket body and including a front portion to extend over at least a portion of the front portion of said bracket body and over at least a portion of an arch wire received in said bracket body to retain said arch wire in said bracket body, and a resilient rear portion connected with said front portion and adapted to be inserted into said passageway, said rear portion comprising means for springingly engaging at least two opposed surface portions of said passageway defining means and for being springingly wedged between and in contact with both of said opposed surface portions of said passageway to retain said rear portion of said retaining device in said passageway with said front portion at least partially covering said arch wire.

2. An orthodontic bracket according to claim 1 wherein said rear portion comprises a generally U-shaped bent-over portion, the legs of said U-shaped bent-over portion being biased away from each other as to be spread apart a distance greater than the width of said passageway behind said bracket body, whereby when said rear portion is inserted in said passageway behind said bracket body, said legs of said U-shaped portion are resiliently moved toward each other and are biased toward opposing walls of said passageway to springingly wedge said rear portion of said retaining device in said passageway with said front portion at least partially covering said arch wire.

3. An orthodontic bracket according to claim 2 wherein a leg of said U-shaped rear portion has a free edge which bitingly engages one of said opposed surface portions to increase retention of said rear portion in said passageway.

4. An orthodontic bracket according to claim 3 wherein said front and rear portions are integrally formed of a spring metal.

5. An orthodontic bracket according to claim 1 wherein said front and rear portions are integrally formed of a spring metal.

6. An orthodontic bracket according to claim 1 wherein said rear portion includes means for connecting auxiliaries thereto.

7. An orthodontic bracket according to claim 6 wherein said auxiliary connecting means comprises at least one aperture in said rear portion.

8. An orthodontic bracket according to claim 2 wherein said auxiliary connecting means comprises at least one aperture in said rear portion.

9. An orthodontic bracket according to claim 8 wherein said aperture is formed in the connecting portion between the legs of said U-shaped portion.

10. An orthodontic bracket according to claim 1 wherein said rear portion comprises a pair of spaced-apart legs having opposing extreme end surfaces which are spaced apart a greater distance than the width of said passageway, said legs being adapted to be resiliently displaced toward each other when being inserted in said passageway and engaging opposed surface portions defining said passageway.

11. An orthodontic bracket according to claim 2 wherein one of said legs of said U-shaped portion comprises a pair of spaced apart members having opposed edges spaced apart a distance greater than the width of said passageway and being resiliently displaceable toward each other when located in said passageway.

12. An orthodontic bracket according to claim 1 wherein said rear portion comprises an irregular surface portion having opposed peak areas which are spaced apart a distance greater than the depth of said passageway and engageable with opposed surfaces defining said passageway.

13. An orthodontic bracket according to claim 12 wherein the rear portion is fabricated of a spring-type metal such that said opposed peak areas are resiliently displaceable toward each other when engaged with said opposed surfaces defining said passageway.

14. A retaining device for use with a bracket having a passageway for receiving a portion of the retaining device, comprising:
   a front portion adapted to engage over at least a part of a portion of a bracket having an arch wire receiving opening therein, and to pass over at least a portion of the arch wire receiving opening to retain an arch wire in a bracket body; and
   a rear portion coupled to said front portion and adapted to be received in the passageway defined by said bracket, said rear portion comprising means for springly engaging at least two opposed surface portions of a passageway of a bracket and for being springingly wedged between and in contact with both of said opposed surface portions of said passageway to be retained in said passageway with said front portion at least partially covering an arch wire receiving opening of a bracket.

15. A retaining device according to claim 14 wherein said rear portion comprises a generally U-shaped bent-over portion, the legs of said U-shaped bent-over portion being biased away from each other so as to be spread apart a distance greater than the width of the passageway of a bracket, whereby when said rear portion is inserted in the passageway of a bracket, said legs of said U-shaped portion are resiliently moved toward each other and are biased toward opposing walls of said passageway to springingly wedge said rear portion of said retaining device in said passageway.

16. A retaining device according to claim 15 wherein a leg of said U-shaped rear portion has a free edge for bitingly engaging one of the opposed surfaces of the passageway.

17. A retaining device according to claim 16 wherein said front and rear portions are integrally formed of spring metal.

18. A retaining device according to claim 14 wherein said front and rear portions are integrally formed of spring metal.

19. A retaining device according to claim 14 wherein said rear portion comprises means for engaging auxiliaries.

20. A retaining device according to claim 19 wherein said auxiliary engaging means comprises at least one aperture in said rear portion.

21. A retaining device according to claim 15 wherein said auxiliary engaging means comprises at least one aperture in said rear portion.

22. A retaining device according to claim 21 wherein said aperture is in the connecting part between the legs of said U-shaped portion.

23. A retaining device according to claim 14 wherein said rear portion comprises a pair of spaced apart legs having opposing extreme end surfaces which are spaced apart a greater distance than the width of said passageway, said legs being adapted to be resiliently displaced toward each other when being inserted in said passageway and engaging opposed surface portions defining said passageway.

24. A retaining device according to claim 15 wherein one of said legs of said U-shaped portion comprises a pair of spaced apart members having opposed edges spaced apart a distance greater than the width of said passageway and being resiliently displaceable toward each other when located in said passageway.

25. A retaining device according to claim 14 wherein said rear portion comprises an irregular surface portion having opposed peak areas which are spaced apart a distance greater than the depth of said passageway engageable with opposed surfaces defining said passageway.

26. A retaining device according to claim 25 wherein the rear portion is fabricated of a spring-type metal such that said opposed peak areas are resiliently displaceable toward each other when engaged with said opposed surfaces defining said passageway.

27. An orthodontic bracket arrangement comprising:
   at least two spaced apart bracket bodies each having means for receiving an arch wire, means for mounting said bracket bodies to a tooth in a spaced-apart relationship, and means defining an elongated passageway at least between the bracket bodies; and
   a retainer member slideably engageable with said bracket bodies and including a front portion which extends over at least a portion of the front portions of said bracket bodies and over at least a portion of an arch wire received in said bracket bodies to retain said arch wire in said bracket bodies, and a resilient rear portion connected with said front portion and adapted to be inserted into said passageway, said rear portion comprising means for springingly engaging at least two opposed surface portions of said passageway defining means and for being springingly wedged between and in contact with both of said opposed surface portions to retain said rear portion of said retaining device in said passageway with said front portion at least partially covering said arch wire.

28. An orthodontic bracket according to claim 27 wherein said rear portion comprises a generally U-shaped bent-over portion, the legs of said U-shaped bent-over portion being biased away from each other so as to be spread apart a distance greater than the width of said passageway, whereby when said rear portion is inserted in said passageway, said legs of said U-shaped portion are resiliently moved toward each other and are biased toward opposing walls of said passageway to springingly wedge said rear portion of said retaining device in said passageway with said front portion at least partially covering said arch wire.

29. An orthodontic bracket according to claim 28 wherein a leg of said U-shaped rear portion has a free edge which bitingly engages one of said opposed surface portion to increase retention of said rear portion in said passageway.

30. An orthodontic bracket according to claim 29 wherein said front and rear portions are integrally formed of a spring metal.

31. An orthodontic bracket according to claim 27 wherein said front and rear portions are integrally formed of a spring metal.

32. An orthodontic bracket according to claim 27 wherein said rear portion includes means for connecting auxiliaries thereto.

33. An orthodontic bracket according to claim 32 wherein said auxiliary connecting means comprises at least one aperture in said rear portion.

34. An orthodontic bracket according to claim 28 wherein said auxiliary connecting means comprises at least one aperture in said rear portion.

35. An orthodontic bracket according to claim 34 wherein said aperture is formed in the connecting portion between the legs of said U-shaped portion.

36. An orthodontic bracket according to claim 27 wherein said rear portion comprises an irregular surface portion having opposed peak areas which are spaced apart, in a direction transverse to the plane of said rear portion, a distance greater than the depth of said passageway and engageable with opposed surfaces defining said passageway.

37. An orthodontic bracket according to claim 36 wherein the rear portion is fabricated of a spring-type metal such that said opposed peak areas are resiliently displaceable toward each other when engaged with said opposed surfaces defining said passageway.

38. An orthodontic bracket according to claim 27 wherein said rear portion is dimensioned relative to said passageway to prevent sidewise movements of said retaining device relative to said brackets.

39. A retaining device for use with a bracket arrangement having at least two spaced-apart bracket bodies and means defining a passageway for receiving a portion of the retaining device, comprising:
 a front portion adapted to engage over at least a part of a portion of a bracket having an arch wire receiving opening therein, and to pass over at least a portion of the arch wire receiving opening to retain an arch wire in a bracket body; and
 a rear portion coupled to said front portion and adapted to be received in the passageway defined by said bracket arrangement, said rear portion comprising means for engaging at least two opposed surface portions of a passageway of the bracket arrangement and for being wedged between and in contact with both of said opposed surface portions of said passageway to be retained in said passageway with said front portion at least partially covering an arch wire receiving opening of a bracket.

40. A retaining device according to claim 39 wherein said rear portion springingly engages at least two opposed surface portions of a passageway of a bracket and is springingly wedged between opposed surface portions of said passageway.

41. A retaining device according to claim 40 wherein said rear portion comprises a generally U-shaped bent-over portion, the legs of said U-shaped bent-over portion being biased away from each other so as to be spread apart a distance greater than the width of said passageway, whereby when said rear portion is inserted in said passageway, said legs of said U-shaped portion resiliently spring toward each other and are biased toward opposing walls of said passageway to springingly wedge said rear portion of said retaining device in said passageway with said front portion at least partially covering said arch wire.

42. A retaining device according to claim 41 wherein a leg of said U-shaped rear portion has a free edge which bitingly engages one of said opposed surface portion to increase retention of said rear portion in said passageway.

43. A retaining device according to claim 42 wherein said front and rear portions are integrally formed of a spring metal.

44. A retaining device according to claim 39 wherein said front and rear portions are integrally formed of spring metal.

45. A retaining device according to claim 39 wherein said rear portion includes means for connecting auxiliaries thereto.

46. A retaining device according to claim 45 wherein said auxiliary connecting means comprises at least one aperture in said rear portion.

47. An orthondontic bracket according to claim 46 wherein said aperture is formed in the connecting portion between the legs of said U-shaped portion.

48. A retaining device according to claim 39 wherein said front portion has portions depending therefrom for engaging the bracket bodies to stabilize the retaining device on the bracket arrangement.

49. A retaining device according to claim 39 wherein said rear portion comprises an irregular surface portion having opposed peak areas which are spaced apart, in a direction transverse to the plane of said rear portion, a distance greater than the depth of said passageway and engageable with opposed surfaces defining said passageway.

50. A retaining device according to claim 49 wherein the rear portion is fabricated of a spring-type metal such that said opposed peak areas are resiliently displaceable toward each other when engaged with said opposed surfaces defining said passageway.

51. A retaining device according to claim 39 wherein said rear portion is dimensioned relative to said passageway to prevent sidewise movements of said retaining device relative to said bracket arrangement.

52. An orthodontic bracket arrangement comprising:
 mounting means for mounting the bracket arrangement to a tooth, said mounting means at least partially defining an elongated passageway, said passageway having opposed surface portions;
 a body portion depending from said mounting means, said body portion having a generally upwardly directed surface portion spaced from said mounting means, said generally upwardly directed surface portion having at least one arch wire receiving opening therein, said arch wire receiving opening facing said mounting means and facing a tooth on which said bracket arrangement is mounted, said generally upwardly directed surface portion having arch wire retaining means extending therefrom and cooperating with said arch wire receiving opening for at least partially engaging an arch wire; and
 a spring clip retaining device of spring-type material extending into said passageway and cooperating with said arch wire receiving opening to retain an arch wire therein, said spring clip retaining device having at least a first member adapted to extend into said passageway and a second member depending from said first member and forming a generally U-shape with said first member;
 said first member of said retaining device including means for springingly engaging said opposed surfaces of said passageway so as to be springingly wedged between and in contact with said opposed surface portions of said passageway.

53. An orthodontic bracket arrangement according to claim 52 wherein said mounting means comprises respective bent portions adjacent said body portion and on each side of said body portion, said bent portions being bent outwardly relative to a tooth on which said bracket arrangement is mounted, each of said bent portions at least partially defining respective passageways into which said rear portion of said retaining device extends.

54. An orthodontic bracket arrangement according to claim 53 wherein said first member of said retaining device comprises means for springingly engaging respective portions of said outwardly bent portions of said mounting means.

55. An orthodontic bracket arrangement according to claim 52 wherein said mounting means comprises means adjacent said body on each side of said body for at least partially defining respective passageways into which at least a portion of said retaining device extends.

56. An orthodontic bracket arrangement according to claim 55 wherein said passageway defining means comprises bent portions bent outwardly relative to the tooth on which the bracket arrangement is mounted for at least partially defining said respective passageways.

57. An orthodontic bracket arrangement according to claim 52 wherein said first member of said retaining device is generally U-shaped and comprises first and second integrally formed legs of spring-type material, said first and second legs being spring biased away from each other, said first and second legs being adapted to be received in said passageways.

58. An orthodontic bracket arrangement according to claim 57 wherein a leg of said first member has a free edge which bitingly engages one of the surface portions defining said respective passageways.

59. An orthodontic bracket arrangement according to claim 57 wherein said retaining device is integrally formed of a spring metal.

60. An orthodontic bracket arrangement according to claim 55 wherein said first member comprises a pair of spaced-apart legs having opposing extreme end surfaces which are spaced apart a greater distance than the width between end surfaces of said passageways, said legs being adapted to be resiliently displaced toward each other by being inserted in said passageways and engaging opposed surface portions defining said passageways.

61. An orthodontic bracket arrangement according to claim 57 wherein said first member comprises an irregular surface portion having opposed peak areas which are spaced apart in a direction perpendicular to the surface of a tooth on which said bracket arrangement is mounted, a distance greater than the depth of said passageways and engageable with opposed surfaces defining said passageways.

62. An orthodontic bracket arrangement according to claim 61 wherein said first member is fabricated of a spring-type metal and said opposed peak areas are resiliently displaceable toward each other when engaged with said opposed surfaces defining said passageways.

63. An orthodontic bracket arrangement according to claim 52 wherein said second member includes at least one contoured surface portion which is contoured to engage at least a surface portion of an arch wire, or the like, inserted in said arch wire receiving openings of said body portion.

64. An orthodontic bracket arrangement according to claim 52 wherein said mounting means and body portion are integrally formed of a single piece of metallic material.

65. An orthodontic bracket arrangement according to claim 52 wherein said mounting means and body portion are integrally formed from a single piece of sheet metal material.

66. A retaining device for use with a bracket arrangement having at least two spaced-apart bracket bodies each having an arch wire receiving opening therein, and means defining a passageway located between said spaced-apart bracket bodies for receiving at least a portion of the retaining device therein, the retaining device comprising:
   front portions adapted to respectively engage over at least a part of a portion of said two spaced-apart bracket bodies and to pass over at least a portion of the respective arch wire receiving openings to retain an arch wire in said bracket bodies; and
   a rear portion coupled to both of said front portions and adapted to be received in the passageway defined by said bracket arrangement, said rear portion comprising means cooperating with said passageway defining means, said cooperating means lockingly engaging said rear portion in said passageway with said front portions at least partially covering the respective arch wire receiving openings of said spaced-apart bracket bodies.

67. A retaining device according to claim 66, wherein said at least part of said rear portion of said retaining device is resilient, and wherein cooperating means includes a protrusion adjacent a free edge thereof and extending generally transverse to the length of said passageway for passing through said passageway and snappingly engaging over an end surface of said passageway.

68. A retaining device according to claim 66, wherein said rear portion of said retaining device is dimensioned relative to the mesial-distal dimension of said passageway so as to prevent mesial-distal movement of said retaining device relative to said bracket bodies.

69. A retaining device according to claim 68, wherein said rear portion of said retaining device has a width which is substantially equal to the width of said passageway in the mesial-distal direction to prevent said mesial-distal movement.

70. A retaining device according to claim 66, wherein said rear portion of said retaining device includes means for springingly engaging opposed surfaces of said passageway so as to be springingly wedged between and in contact with said opposed surface portions of said passageway.

71. A retaining device according to claim 66, wherein said rear portion of said retaining device comprises first and second integrally formed legs of spring-type material, said first and second legs being spring biased away from each other and being adapted to be received in said passageway and springingly engaging opposing surfaces of said passageway.

72. A retaining device according to claim 66, wherein said rear portion of said retaining device is bowed to present a concave surface portion spaced from a surface of said passageway defining means, said space between said concave portion and said surface of said passageway defining means comprising an access channel for passing auxiliaries, or the like, therethrough.

73. A retaining device for use with a bracket arrangement having at least one bracket body and means defining a passageway for receiving a portion of the retaining device, comprising:
   a front portion adapted to engage over at least a portion of a bracket body having an arch wire receiving opening therein, and to pass over at least a portion of the arch wire receiving opening to retain an arch wire in the bracket body; and a rear portion coupled to said front portion and adapted to be received in the passageway defined by said bracket arrangement, said rear portion comprising means cooperating with said passageway defining means for retaining said rear portion in said passageway with said front portion at least partially covering an arch wire receiving opening of a bracket, said rear portion being bowed to present a concave surface portion spaced from a surface of said passageway defining means, said space between said concave surface portion and said surface of said passageway defining means defining an access channel in said passageway for passing of auxiliaries, or the like, therethrough.

74. A retaining device according to claim 73 wherein said rear portion comprises means cooperating with said passageway for substantially preventing mesial-distal movement of said retaining device relative to said bracket body.

75. A retaining device according to claim 73, wherein the concave portion of said rear portion engages a surface of said passageway defining means, and the ends of said rear portion remote from said concave portion and which extend in the same direction as said concave portion engaging an opposite surface portion of said passageway defining means to substantially prevent mesial-distal movement of said retaining device relative to said bracket body.

76. A retaining device according to claim 75, wherein said rear portion is made of spring-type material and said edges and concave portion are springingly wedged between said opposite surfaces of said passageway defining means.

77. A retaining device according to claim 73, wherein said front and rear portions are connected together in a generally U-shape, the connecting portion of said U-shaped device having a cut-out portion.

78. A retaining device for use with a bracket arrangement having at least one bracket body and means defining a passageway for receiving a portion of the retaining device, comprising:
a front portion adapted to engage over at least a portion of a bracket body having an arch wire receiving opening therein, and to pass over at least a portion of the arch wire receiving opening to retain an arch wire in the bracket body; and
a rear portion coupled to said front portion and adapted to be received in the passageway defined by said bracket arrangement, said rear portion comprising means cooperating with said passageway defining means for retaining said rear portion in said passageway with said front portion at least partially covering an arch wire receiving opening of a bracket, said rear portion having a void area such that at least a portion of said rear portion does not fill the complete width of said passageway in the mesial-distal direction of said passageway, said rear portion at least partially defining, with said passageway defining means, an access channel in said passageway for passing of auxiliaries therethrough.

79. A retaining device according to claim 78, wherein said rear portion includes means for engaging and guiding auxiliaries, or the like, through said access channel.

80. A retaining device according to claim 78, wherein said void portion is intermediate the side of said rear portion.

81. A retaining device according to claim 78, wherein said void portion is at least a portion of a side of said rear portion.

82. A retaining device according to claim 81, wherein said rear portion of said retaining device comprises first and second members which are connected together in a generally U-shaped, one of said first and second members having a width which is substantially equal to the width of said passageway in the mesial-distal direction of said passageway to substantially prevent mesial-distal movement of said retaining device relative to said bracket body, the other of said members having a width which is less than the width of said first-mentioned member, whereby auxiliaries may be received in the portion of said passageway left unoccupied by said shorter width other member.

83. A retaining device according to claim 80, wherein said rear portion comprises first and second members connected together in a generally U-shape, said void portion being formed in one of said first and second members.

84. A retaining device according to claim 78 wherein said void portion extends the length of said passageway.

85. A retaining device according to claim 78, wherein said rear portion comprises means cooperating with said passageway for substantially preventing mesial-distal movement of said retaining device relative to said bracket body.

86. A retaining device according to claim 85, wherein said void portion is intermediate the sides of said rear portion.

87. A retaining device according to claim 86, wherein said rear portion comprises first and second members connected together in a generally U-shaped, said void portion being formed in one of said first and second members.

88. A retaining device according to claim 85, wherein said void portion is at least a portion of a side of said rear portion.

89. A retaining device according to claim 88, wherein said rear portion of said retaining device comprises first and second members which are connected together in a generally U-shape, one of said first and second members having a width which is substantially equal to the width of said passageway in the mesial-distal direction of said passageway to substantially prevent mesial-distal movement of said retaining device relative to said bracket body, the other of said members having a width which is less than the width of said first-mentioned member, whereby auxiliaries may be received in the portion of said passageway left unoccupied by said shorter width other member.

90. A retaining device for use with a bracket arrangement having at least one bracket body and means defining a passageway for receiving a portion of the retaining device, comprising:
a front portion adapted to engage over at least a portion of a bracket body having an arch wire receiving opening therein, and to pass over at least a portion of the arch wire receiving opening to retain an arch wire in the bracket body; and
a rear portion coupled to said front portion and adapted to be received in the passageway defined by said bracket arrangement, said rear portion comprising first and second members connected together in a generally U-shape, said rear portion cooperating with said passageway defining means for retaining said rear portion in said passageway with said front portion at least partially covering an arch wire receiving opening of a bracket, at least one of said first and second members extending in the mesial-distal direction of said passageway to an extent substantially equal to the width of said passageway for substantially preventing mesial-distal movement of said retaining device relative to said bracket body and at least the other of said first and second members having a void portion in the mesial-distal direction of said passageway for at least partially defining an access channel in said passageway for passing of auxiliaries, or the like, therethrough.

91. A retaining device according to claim 90, wherein said void portion is intermediate the sides of at least said other of said first and second members.

92. A retaining device according to claim 90, wherein said void portion is at least a portion of a side of at least said other of said first and second members.

93. A retaining device according to claim 90, wherein said void portion extends the length of said passageway.

94. A retaining device according to claim 66, wherein said rear portion of said retaining device is located intermediate the two portions of said front portion which engage over the arch wire receiving openings of said bracket bodies in the mesial-distal direction of said bracket arrangement.

* * * * *